(12) United States Patent
Gwak

(10) Patent No.: US 12,161,224 B2
(45) Date of Patent: Dec. 10, 2024

(54) POSTURE CORRECTING APPARATUS

(71) Applicant: Taeyeong Gwak, Daegu (KR)

(72) Inventor: Taeyeong Gwak, Daegu (KR)

( * ) Notice: Subject to any disclaimer, the term of this patent is extended or adjusted under 35 U.S.C. 154(b) by 940 days.

(21) Appl. No.: 17/068,610

(22) Filed: Oct. 12, 2020

(65) Prior Publication Data

US 2021/0022503 A1 Jan. 28, 2021

Related U.S. Application Data

(63) Continuation of application No. PCT/KR2019/010423, filed on Aug. 16, 2019.

(30) Foreign Application Priority Data

Aug. 22, 2018 (KR) .................. 10-2018-0098089
Aug. 14, 2019 (KR) .................. 10-2019-0099928

(51) Int. Cl.
*A47B 97/00* (2006.01)
*F16M 11/14* (2006.01)

(52) U.S. Cl.
CPC ............. *A47B 97/00* (2013.01); *F16M 11/14* (2013.01)

(58) Field of Classification Search
CPC ....... A47C 16/00; A47C 31/126; A47C 31/12; A61B 5/1116; A61B 5/11; F16M 11/40; F16M 11/14; F16M 11/046; F16M 11/10; F16M 11/2021; F16M 11/2092; F16M 11/28; F16M 13/022; A47B 97/00; A47B 95/00; A61G 5/1075; A61F 5/05883; A61F 5/01; G08B 3/10
See application file for complete search history.

(56) References Cited

U.S. PATENT DOCUMENTS

| 4,650,249 A | * | 3/1987 | Serber ................. A47C 9/005 248/397 |
| 5,542,746 A | * | 8/1996 | Bujaryn ............... A47C 9/005 297/301.1 |
| 9,770,110 B1 | * | 9/2017 | Biggs ................... A47C 16/00 |
| 2012/0187727 A1 | | 7/2012 | Wu |
| 2013/0232696 A1 | * | 9/2013 | Halimi ................ A47C 16/00 5/640 |

FOREIGN PATENT DOCUMENTS

| CN | 201452146 U | | 5/2010 | |
| CN | 105411220 A | | 3/2016 | |
| GB | 2395112 A | * | 5/2004 | ............. A47C 16/00 |
| JP | S46-10917 Y | | 4/1971 | |
| JP | 3010376 U | * | 5/1995 | |
| JP | 3015432 U | | 9/1995 | |

(Continued)

OTHER PUBLICATIONS

International Search Report issued in PCT/KR2019/010423; mailed Nov. 22, 2019.

*Primary Examiner* — Ophelia A Hawthorne
(74) *Attorney, Agent, or Firm* — Studebaker & Brackett PC

(57) ABSTRACT

Disclosed is a posture correction device. According to the present invention, the posture correction device includes: a base part; and a recognizing part having a frame whose one side is coupled to the base part in such a manner as to allow one or more of a height and an angle to be adjusted, wherein the recognizing part is recognized visually and tactilely according to a user's posture.

17 Claims, 14 Drawing Sheets

(56) References Cited

FOREIGN PATENT DOCUMENTS

| | | | |
|---|---|---|---|
| JP | 2018033878 A | * | 3/2018 |
| KR | 10-2020-0116152 A | | 10/2010 |
| KR | 10-1449665 B1 | | 10/2014 |
| KR | 10-1546249 B1 | | 8/2015 |
| KR | 10-2015-0129471 A | | 11/2015 |
| WO | 2012/050319 A2 | | 4/2012 |

* cited by examiner

Range of vision

POSTURE CORRECTING APPARATUS

CROSS-REFERENCE TO RELATED APPLICATIONS

The present application is a continuation of International Patent Application No. PCT/KR2019/010423, filed on Aug. 16, 2019, which is based upon and claims the benefit of priority to Korean Patent Application Nos. 10-2018-0098089 filed on Aug. 22, 2018, 10-2019-0099928 filed on Aug. 14, 2019. The disclosures of the above-listed applications are hereby incorporated by reference herein in their entirety.

TECHNICAL FIELD

The present invention relates to a posture correction device.

BACKGROUND ART

Recently, spinal pain, especially, neck and back pain may affect people of any age due to their bad posture in which they excessively bend their neck forward, have a bent waist, and move their hips too far forward or backward. Further, such pain is caused by bad posture in which people feel comfortable unconsciously, and also, it is caused by bad posture which is bad objectively but good subjectively.

Generally, a student or worker who sits at a desk to study or work has a bad posture in which his or her back is bent or his or her neck cranes forward, for long hours, and in this case, his or her bad posture becomes his or her posture habit.

If he or she keeps his or her bad posture due to the posture habit, a load is concentrated on his or her back to thus cause various physical problems, such as lumbar or cervical herniated disk, scoliosis, and so on.

Accordingly, there is a definite need to develop a posture correction device capable of allowing a student or worker who sits at a desk to study or work to have his or her good neck, back, waist, and hip postures.

DISCLOSURE

Technical Problem

Accordingly, the present invention has been made to solve the above-mentioned problems, and it is an object of the present invention to provide a posture correction device that is capable of utilizing a space between a desk and a user to obtain a visual or tactile signal, thereby preventing him or her from taking a bad posture unconsciously or for his or her comfort.

Technical Solution

To accomplish the above-mentioned objects, according to the present invention, there is provided a posture correction device including: a base part; and a recognizing part having a frame whose one side is coupled to the base part in such a manner as to allow one or more of a height and an angle to be adjusted, wherein the recognizing part is recognized visually and tactilely according to a user's posture.

The posture correction device further includes a contact part coupled to one side of the base part in such a manner as to protrude toward the user's abdomen.

The contact part is slidably coupled to both sides of the base part in such a manner as to be adjusted in a length protruding from the base part toward the user's abdomen.

The contact part comprises slide slots formed on both sides of the base part in a longitudinal direction of the base part; one pair of sliders slidable forward and backward along the slide slots; slider fixing means adapted to fix one pair of sliders to the slide slots; and an abdomen contact member adapted to connect ends of one pair of sliders to each other in such a manner as to come into contact with the user's abdomen.

The posture correction device further comprises coupling means located rotatable to left and right sides on the base part in such a manner as to be coupled to one side of the frame to allow the recognizing part to be pivoted in left and right directions with respect to the user.

The base part has a suction pad located on the underside thereof.

The base part comprises an upper plate coupled to the recognizing part; a lower plate located on the underside of the upper plate; and fastening means for fastening the upper plate and the lower plate to a piece of furniture.

The recognizing part is made of a flexible material capable of being adjusted in height and angle thereof.

The recognizing part is constituted of a plurality of different-sized support tubes capable of being adjusted in height thereof.

The recognizing part further comprises a support tube coupled to the base part; and a recognizing support tube having a given angle with respect to the support tube by means of an articulation.

The recognizing part further comprises at least one or more elastic members located on the plurality of support tubes to allow the recognizing part to tilt in one direction by means of an external force and to be returned to an original position thereof if the external force is released.

The recognizing part further comprises a visual/tactile checking member coupled to the other side end portion of the frame in such a manner as to be located under the user's chin or around the user's neck and to be thus recognized visually or tactilely according to the user's posture.

The recognizing part further comprises an upper body posture checking member connected to the frame in such a manner as to be located around the user's upper body under the user's neck if the visual/tactile checking member is located under the user's chin or around the user's neck.

The recognizing part further comprises a string or frame connected to the other side end portion of the frame in such a manner as to located under the visual/tactile checking member; and an upper body posture checking member provided on the end of the string or frame in such a manner as to be located around the user's upper body under the user's neck if the visual/tactile checking member is located under the user's chin or around the user's neck.

The recognizing part further comprises a contact frame whose one side is coupled to the frame in such a manner as to protrude toward the user's upper body; and an upper body posture checking member provided on the other side end portion of the contact frame in such a manner as to be located around the user's upper body under the user's neck if the visual/tactile checking member is located under the user's chin or around the user's neck.

The posture correction device further includes a distance sensor located on the visual/tactile checking member to measure a distance from the user; an alarming member for generating an alarm to the user; and a controller for controlling the alarming member on the basis of the measured distance through the distance sensor.

The recognizing part further comprises a main support tube whose one side is coupled to the base part and the other side is coupled to an articulation to have a given angle with respect to the frame, the main support tube comprising: a first main support tube coupled to the base part; a second main support tube coupled to the first main support tube; and a third main support tube coupled to the second main support tube and having a hollow portion adapted to insert an elastic member thereinto, the elastic member being inserted into the hollow portion of the third main support tube in such a manner as to allow one side thereof to be connected to the articulation and the other side thereof to be connected to the second main support tube.

The other side of the third main support tube has one shape of a sphere, triangle, and square, and the articulation has a corresponding shape to the other side of the third main support tube in such a manner as to be seated onto the other side of the third main support tube.

The recognizing part is coupled to the base part in such a manner as to allow one side thereof to be detachably mounted on the base part.

Advantageous Effects

According to the present invention, the posture correction device can utilize a space between a desk and a user to obtain a visual or tactile signal, so that if he or she takes a bad posture unconsciously or for his or her comfort, he or she can immediately recognize his or her bad posture, thereby continuously correcting the bad posture to take good posture habit.

MODE FOR INVENTION

Hereinafter, the present invention will now be described in detail with reference to the attached drawings. Before the present invention is disclosed and described, it is to be understood that the disclosed embodiments are provided to generally understand methods, devices and/or systems as will be described below. However, the disclosed embodiments are merely exemplary of the invention, and the present invention is not limited thereto.

In the description of the invention, if it is determined that the detailed explanation on the well known technology related to the present invention makes the scope of the present invention not clear, the explanation will be avoided for the brevity of the description. Further, the terms as will be discussed later are defined in accordance with the functions of the present invention, but may be varied under the intention or regulation of a user or operator. Therefore, they should be defined on the basis of the whole scope of the present invention. The terminology used herein is for the purpose of describing particular embodiments only and is not intended to be limiting.

An expression referencing a singular value additionally refers to a corresponding expression of the plural number, unless explicitly limited otherwise by the context. In this application, terms, such as "comprise", "include", or 'have", are intended to designate those characteristics, numbers, steps, operations, elements, or parts which are described in the specification, or any combination of them that exist, and it should be understood that they do not preclude the possibility of the existence or possible addition of one or more additional characteristics, numbers, steps, operations, elements, parts or combinations thereof, or possibilities.

Figure 1:
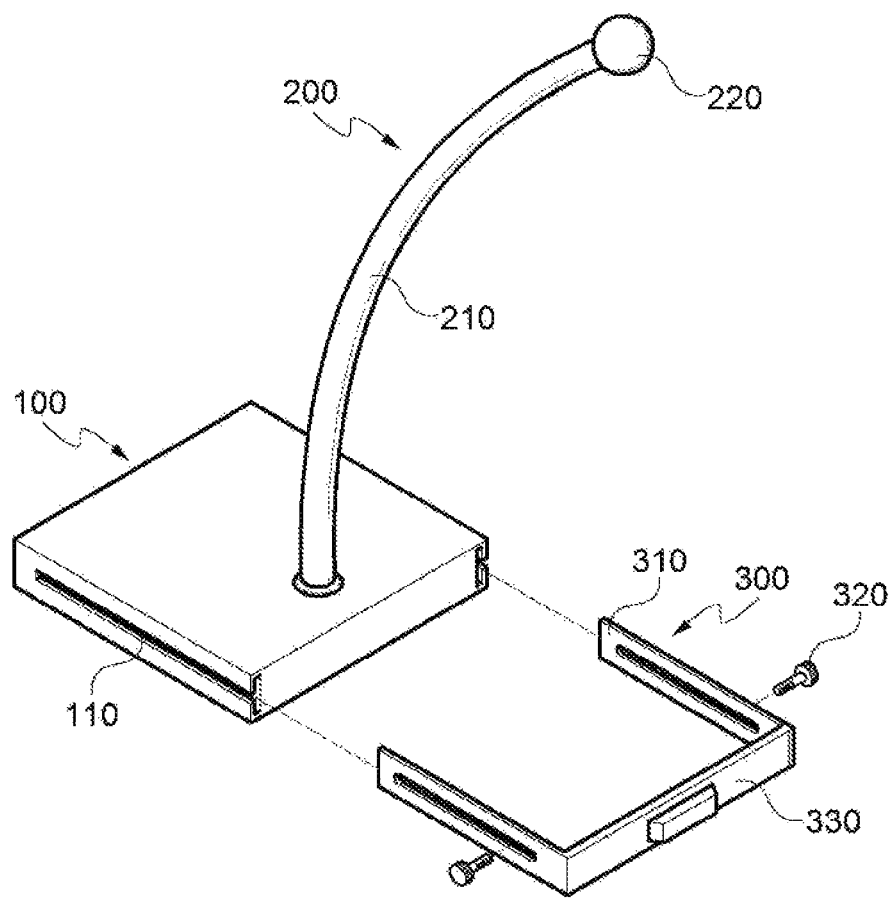
FIG. 1 is a perspective view showing a posture correction device according to a first embodiment of the present invention.

As shown in FIG. 1, a posture correction device 10 according to a first embodiment of the present invention includes a base part 100, a recognizing part 100, and a contact part 300.

The base part 100 is adapted to fix the posture correction device 10 to a given structure (for example, table, desk, book shelf, chair arm rest, chair back, or the like) and has various shapes such as hexahedron, cylinder, and so on.

According to the present invention, the base part 100 can be fixedly erected on a desk or book shelf, and it has a given weight so that it cannot fall down even if a user who sits on a chair with a bad posture comes into contact with the posture correction device 10.

Further, the base part 100 has slide slots 110 formed along both sides thereof in a longitudinal direction in such a manner as to allow the contact part 300 to be slidably coupled thereto.

Furthermore, the base part 100 has coupling means (not shown) rotatable to a left and right, front and back, or diagonal direction or an angle of 360°.

The coupling means is coupled to one side of the recognizing part 200 to allow the recognizing part 200 and the base part 100 to be connected to each other.

In addition, the coupling means is constituted of at least one or more pivoted articulations to allow the recognizing part 200 to rotate to the left and right, front and back, or diagonal direction or the angle of 360° with respect to a user.

Only if the coupling means rotates to the left and right, front and back, or diagonal direction or the angle of 360° to allow a visual/tactile checking member 220 to be located under the user's chin or around his or her neck, it also may have various known structures such as a bearing, universal joint, tooth, ball joint, and so on.

By the way, the posture correction device 10 according to the first embodiment of the present invention is provided with the base part 100 as the erected fixing means, but it may be not limited thereto.

Figure 2:
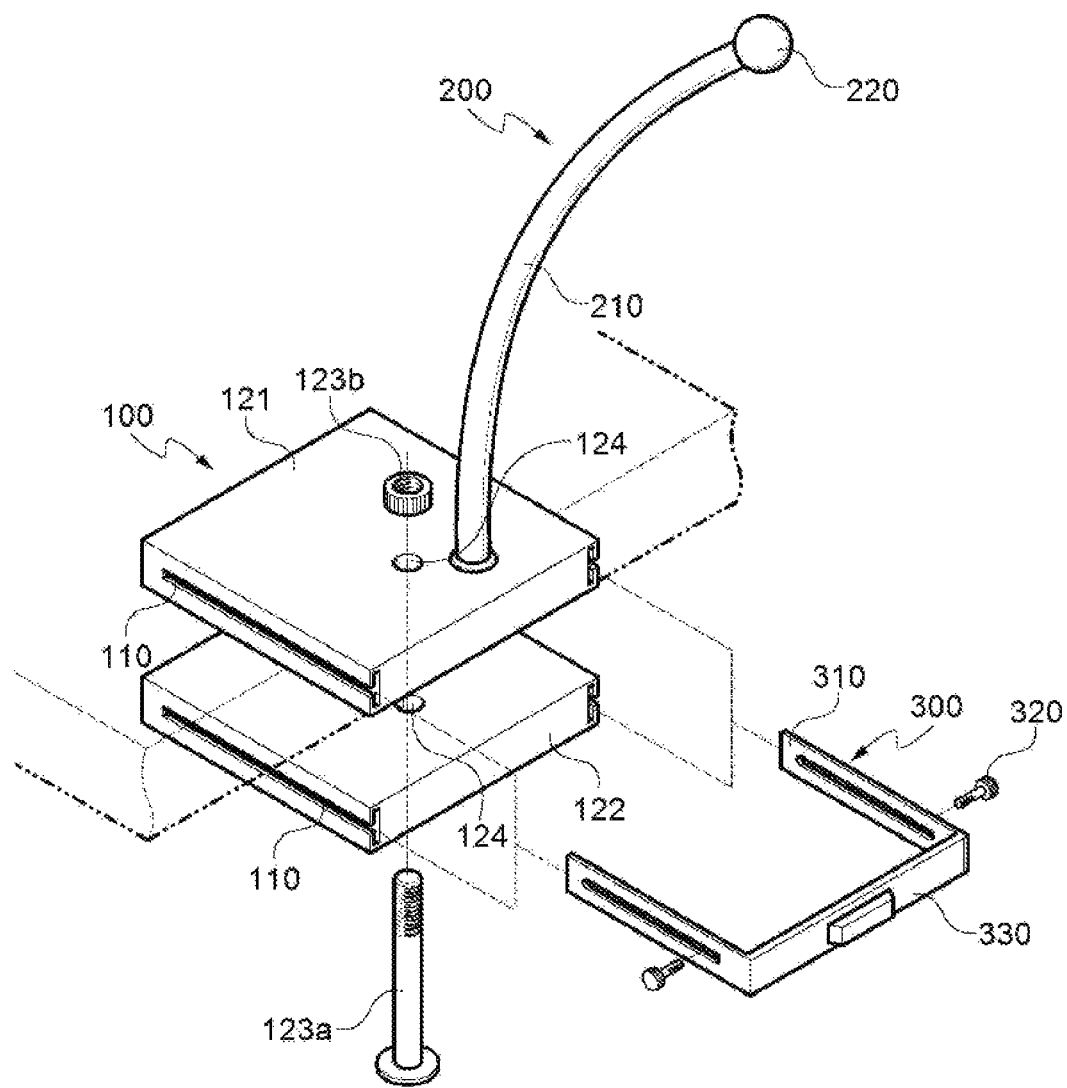
FIG. 2 is a perspective view showing another example of a base part of the posture correction device according to the first embodiment of the present invention.

As shown in FIG. 2, the base part 100 includes an upper plate 121, a lower plate 122, and fastening means 123 for fastening the upper plate 121 and the lower plate 122 to a piece of furniture.

Further, screw insertion holes 124 are formed on given areas of the upper plate 121 and the lower plate 122, and the slide slots 110 are formed on both sides of the upper plate 121 and the lower plate 122 in the longitudinal direction of the base part 100, so that the contact part 300 can slide along the slide slots 110 of the upper plate 121 or the lower plate 122.

The fastening means 123 is constituted of a bolt 123a and a nut 123b. The nut 123b is fastened to the bolt 123a that passes through the screw insertion grooves 123 in such a manner as to be extended to top of the upper plate 121 from the lower plate 122, so that the base part 100 can be coupled to the piece of furniture.

Further, the base part 100 has a suction pad (not shown) located on the underside thereof. The base part 100 is fixed to the piece of furniture by means of the suction pad, thereby reducing the weight of the posture correction device 10 and being conveniently attached to the piece of furniture with ease.

Referring back to FIG. 1, the recognizing part 200 is connected to the base part 100 to allow the user to recognize whether his or her posture is good or bad. Further, the recognizing part 200 is coupled to the coupling means of the base part 100 and is thus connected to the base part 100 to allow the user to recognize whether his or her posture is good or bad. The recognizing part 200 has a frame 210 whose one side is coupled to the base part 100 and the other side is recognized visually or tactilely according to the user's posture.

On the other hand, the recognizing part 200 is connected to the base part 100, but of course, it may be detachably mounted on the base part 100, without being limited thereto.

The frame 210 is adjustable in angle and height. In detail, the frame 210 can rotate to left and right, front and back, or an angle of 360°.

The frame 210 has a shape of a bar having a cylindrical, oval, square, or polygonal section and is flexible so that its changed shape can be maintained by the user's force, thereby providing various heights and angles needed for the user. In this case, the frame 210 can allow the visual/tactile checking member 220 to be easily fixed to the user's desired position.

The frame 210 is twisted or bent so that it can be freely changed in shape, and only if the frame 210 can maintain the changed shape, it may have various known structures.

For example, the frame 210 is constituted of a metal tube that is freely bent and changed in shape, like a copper tube, and otherwise, the frame 210 is constituted of a cobra tube made by spirally winding a metal plate and a metal wire.

Further, the recognizing part 200 includes the visual/tactile checking member 220 located on the other side end portion of the frame 210.

The visual/tactile checking member 220, which is located on the other side end portion of the frame 210, can be placed under the user's chin or around his or her neck through the adjustment of height and angle of the frame 210.

In detail, the visual/tactile checking member 220 is placed under the user's chin or around his or her neck and is thus recognized by the user's visual or tactile sense to allow the user to recognize his or her bad posture. Only if the visual/tactile checking member 220 can be recognized by the user's visual or tactile sense, it may be not limited to a shape, size, and material thereof.

The contact part 300 is coupled to one side surface of the base part 100 in such a manner as to protrude toward the user's abdomen.

Figure 9:
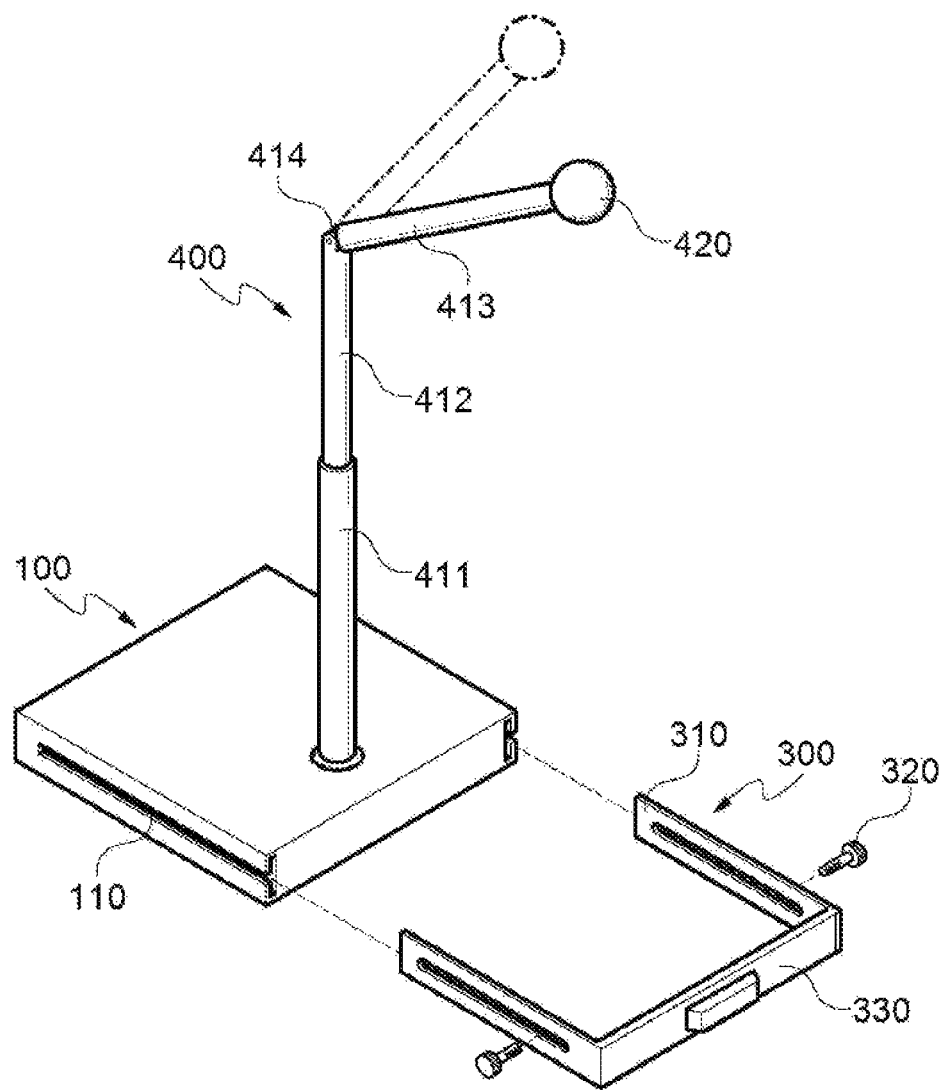
FIG. 9 is a perspective view showing a posture correction device according to a second embodiment of the present invention.

The contact part 300 includes sliders 310 slidable forward and backward along the slide slots 110 formed on both sides of the base part 100, slider fixing means 320 adapted to fix the sliders 310 to the slide slots 110, and an abdomen contact member 330 adapted to connect the sliders 310 to each other in such a manner as to come into contact with the user's abdomen. In some embodiments, the slider fixing means 320 is a bolt screw, as shown in FIG. 9.

The contact part 300 is slidably coupled to the slide slots 110 formed on both sides of the base part 100 in the longitudinal direction of the base part 100 in such a manner as to protrude toward the user's abdomen, and further, the lengths of the sliders 310 in forward and backward directions are adjusted by means of the slider fixing means 320, thereby controlling the protruding length of the abdomen contact member 330.

The contact part 300 can allow the contact between the abdomen contact member 330 and the user to be recognized by the user's tactile sense. Even if the user does not receive any signal through the recognizing part 200 in a state where his or her buttocks excessively push back or his or her upper body or neck is excessively craned forward, he or she can rapidly and accurately recognize his or her bad posture through the contact or non-contact between the contact part 300 and his or her abdomen.

Figure 3:
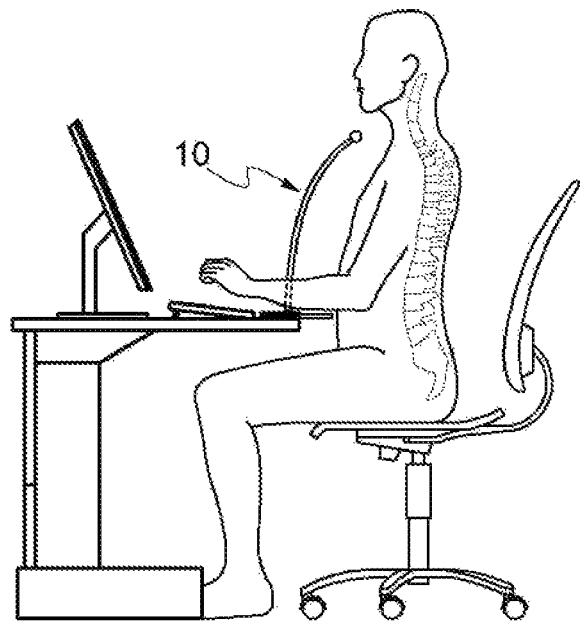
FIG. 3 is a perspective view showing a person's sitting posture on a chair through the posture correction device according to the first embodiment of the present invention.

As shown in FIG. 3, the user has a good posture, and next, the frame 210 is adjusted to allow the recognizing part 200 to be located under his or her chin or around his or her neck, so that the posture correction device 10 according to the present invention can be used in a right manner.

Figure 4:
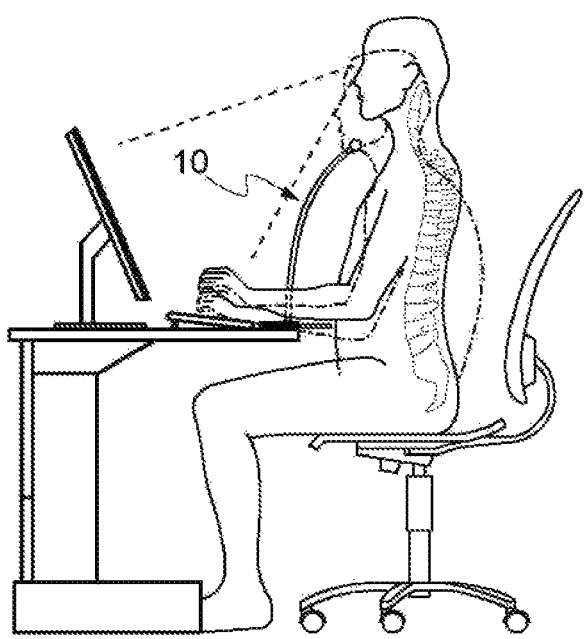
FIG. 4 is a perspective view showing examples of a user's good or bad postures, while using the posture correction device according to the first embodiment of the present invention.
Figure 5:
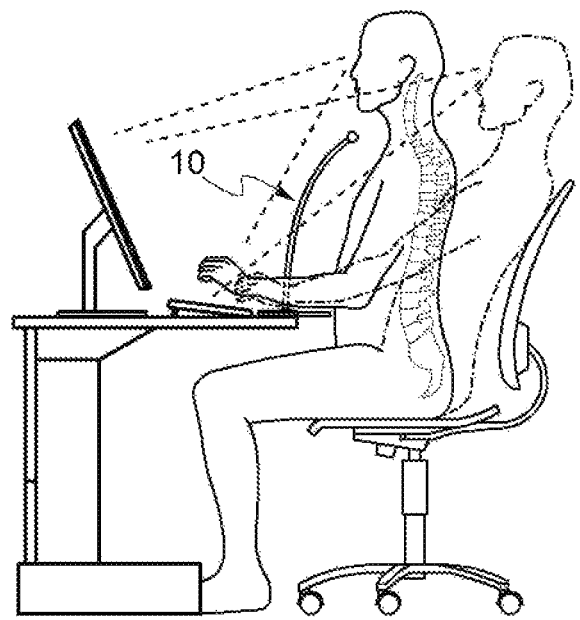
FIG. 5 is a perspective view showing other examples of the user's good or bad postures, while using the posture correction device according to the first embodiment of the present invention.
Figure 6:
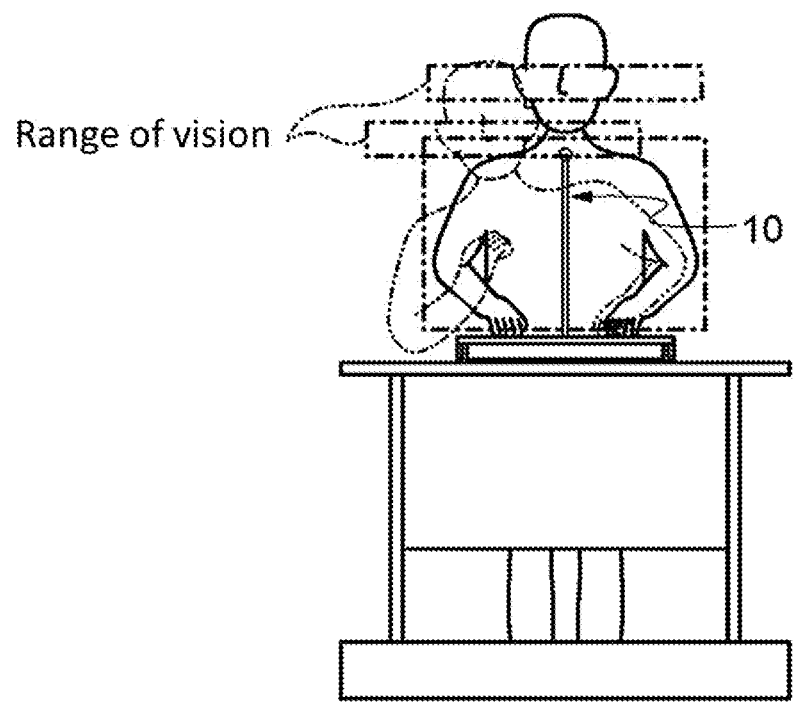
FIG. 6 is a perspective view showing still other examples of the user's good or bad postures, while using the posture correction device according to the first embodiment of the present invention.

Referring to FIG. 4, if the user is bent at the waist, the recognizing part 200 comes into contact with his or her neck, and referring to FIG. 5, if the user's back leans onto a chair back to cause his or her buttocks to be moved toward the desk (that is, he or she pushes his or her waist forward and his or her back leans back), the recognizing part 200 becomes located in front of his or her eyes. Referring to FIG. 6, further, if the user leans to a left (or right) side, the recognizing part 200 becomes located on the right (or left) side of the user. Accordingly, his or her bad posture he or she currently has can be rapidly and accurately recognized by means of the recognizing part 200.

Figure 7:
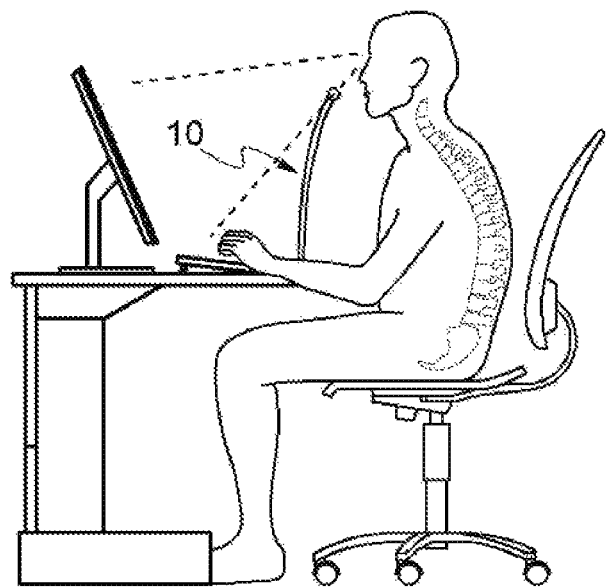
FIG. 7 is s a perspective view showing another example of the user's bad posture generally often taken, while using the posture correction device according to the first embodiment of the present invention.

Referring now to FIG. 7, if a student or worker who sits at a desk to study or work has a bad posture in which his or her back is bent or his or her neck cranes forward, which is frequently taken, the recognizing part 200 is located in front of the user's vision, so that he or she can recognize his or her current bad posture immediately and accurately.

As shown in FIGS. 3 to 7, accordingly, the base part 100 is fixed to the desk as the piece of furniture in such a manner as to allow the posture correction device 10 to be located in front of the user, but of course, the base part 100 may be located beside the user, without being limited thereto.

Figure 8:
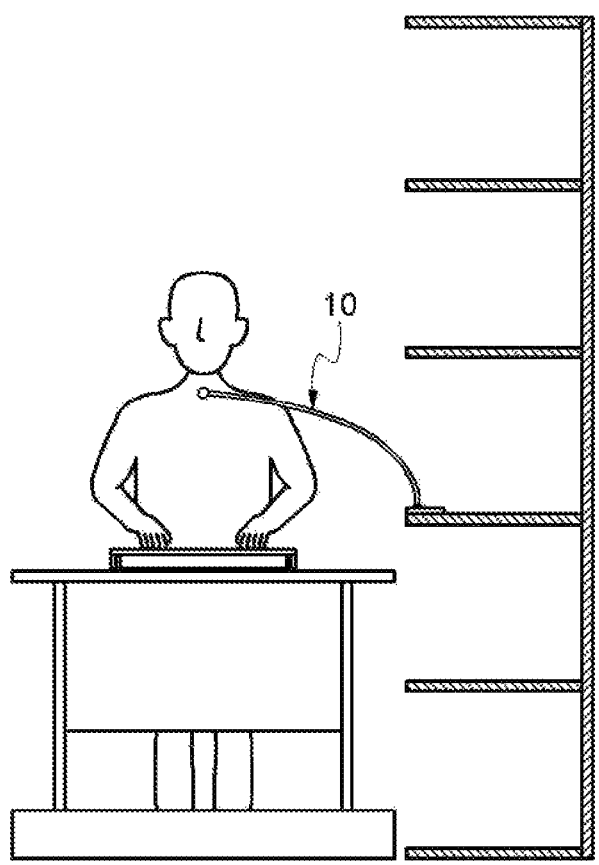
FIG. 8 is a perspective view showing another application example of the posture correction device according to the first embodiment of the present invention.

Referring to FIG. 8, the base part 100 is fixed to a book shelf as a piece of furniture in such a manner as to allow the posture correction device 10 to be located beside the user or at a diagonal position with respect to the user, and the frame 210 is adjusted to allow the recognizing part 200 to be located under his or her chin or around his or her neck, so that the posture correction device 10 can be used in a right manner.

A method for using the posture correction device 10 according to the first embodiment of the present invention will be explained below.

First, the user takes a good posture (his or her cervical and lumbar spines is in a lordosis (excessive inward curve) state, while his or her upper body is being vertical, without leaning forward).

Next, if the user has a forward head posture, the recognizing part 200 comes into contact with his or her neck or comes into view, but the height and angle of the frame 210 can be adjusted so that in a good posture, no visual or tactile signal is received from the recognizing part 200.

It is possible that the recognizing part 200 is located more deeply under the user's chin if necessary.

In the good posture, the contact part 300 does not come into contact with the user's abdomen but comes into contact with the user's abdomen only if he or she slightly pushes his or her abdomen intentionally. In this case, he or she does not push his or her abdomen through breathing, and his or her spine is bent in a little bit larger angle than that in a normal posture, so that his or her waist leans forward, thereby recognizing the contact part 300 through the tactile sense with respect to his or her abdomen.

If the desk is curved, the user works at a long distant position from the deck, or the user is distant from the desk according to the user's chair or his or her physical characteristics, the contact part 300 can provide the tactile sense appropriate to the user's environment through the adjustment of length, and instead of the contact part 300, of course, the user's waist or hip position can be checked by means of the base part 100 or the edge of the desk. In this case, the contact part 300 may be fixed or separated and thus kept in a separate place, without any protrusion.

Accordingly, the user who has the good posture does not receive any visual or tactile signal from the recognizing part 200. In detail, when the user has the good posture, the recognizing part 200 is located at a position where it comes into contact with the user's neck if he or she has a forward head posture, and the base part 100 or the contact part 300 is located at a position where it comes into contact with the user's abdomen if he or she slightly pushes his or her abdomen forward intentionally.

If the user's neck has a good posture but is bent at the waist, the recognizing part 200 is seen just in front of the user or comes into contact with not his neck, but his chin. In a process where a good neck posture is taken, accordingly, a good waist posture can be naturally induced, so that his or her waist posture as well as his or her neck posture can be corrected.

If the user's upper body or neck is inclined to a left or right side, the recognizing part 200 is seen at the right or left side of the user, so that the user can recognize his or her inclined state. Further, if the user leans backward to cause his or her upper body to be bent backward, the recognizing part 200 is seen in front of the user in a state of being a little distant from him or her, so that he or she can recognize his or her upper body is bent backward.

Even in a state where no signal is received from the recognizing part 200, if the user's waist or hip is excessively moved back, his or her upper body or neck becomes excessively moved forward. So as to avoid such a state, accordingly, the user slightly moves his or her abdomen forward frequently to check whether the abdomen comes into contact with the contact part 300 or the base part 100, thereby preventing his or her waist from being moved too far backward.

In detail, if the recognizing part 200 comes into contact with the user's neck or comes into view, or if the user cannot feel any tactile sense when he or she slightly pushes out his or her abdomen, he or she is in a bad posture, which can be recognized by him or her.

The tactile signal of the contact part 300 is also recognized in the same manner as above. Initially, the tactile signal is forgotten or the number of tactile signal recognizing times is small. As the user's neck and spine postures are corrected consciously or unconsciously by means of the recognizing part 200, also, he or she naturally keeps his or her mind in his or her hip position.

In detail, the posture correction device 10 according to the first embodiment of the present invention provides the reference of the good posture for the user to allow him or her to continuously and immediately recognize his or her posture, thereby preventing his or her bad posture from being understood as the good posture.

As mentioned above, the posture correction device 10 according to the first embodiment of the present invention is configured to allow the user to take a good posture for himself or herself, unlike other posture correction devices in which a good posture is physically forced or supported.

Accordingly, the posture correction device 10 according to the first embodiment of the present invention provides the reference of the good posture around the user's neck or chest to allow him or her to continuously and immediately recognize his or her posture and has the good posture accurately, only with one operation, without any adjustment in his or her posture several times, thereby preventing his or her bad posture from being understood as the good posture.

Also, the posture correction device 10 according to the first embodiment of the present invention is located at the outside of the user's body and does not correct his or her posture through the application of a physical force to his or her body, thereby solving the problems occurring in a process of relying on an external physical force.

Further, the posture correction device 10 according to the first embodiment of the present invention does not correct his or her posture through the application of the external physical force to his or her body, so that he or she can be freely moved.

FIG. 9 is a perspective view showing a posture correction device according to a second embodiment of the present invention. The corresponding parts of the second embodiment of the present invention to those of the first embodiment of the present invention as shown in FIGS. 1 and 2 have the same or similar functions as or to those in the first embodiment of the present invention, and accordingly, the repeated explanation on the corresponding parts will be avoided.

First, a recognizing part 400 is constituted of a plurality of different-sized support tubes having a shape of a bar having a cylindrical, oval, square, or polygonal section.

Also, the recognizing part 400 has a plurality of articulations. In this case, the recognizing part 400 has one articulation 414, but it may have two or more articulations, without being limited thereto.

As shown in FIG. 9, the recognizing part 400 in the posture correction device according to the second embodiment of the present invention includes two erected support tubes 411 and 412 having different diameters from each other, a recognizing support tube 413 whose one side is coupled to the articulation 414 in such a manner as to have a given angle with respect to the support tube 412, and a visual/tactile checking member 420 located on the other side of the recognizing support tube 413, and the two erected support tubes 411 and 412 are the lower support tube 411 coupled to a base part 100 and the upper support tube 412 fitted to the lower support tube 411, so that they can be adjusted in height in up and down directions. The visual/tactile checking member 420 can be recognized by means of visual or tactile sense according to the user's posture.

In this case, every user has different use environments and various shapes of abdomens and chests, and accordingly, the number of support tubes adjustable in height in the up and down direction and the number of articulations adapted to pivot the respective support tubes in forward and backward directions are increased or decreased in the recognizing part 400, thereby constituting the recognizing part 400 with more freely shapes.

In addition to the pivot structure, further, only if the articulation 414 rotates to a left and right, front and back, or diagonal direction or an angle of 360°, it may have known structures such as a bearing, universal joint, tooth, ball joint, and so on.

In detail, the articulation 414 rotates to the left and right, front and back, or the angle of 360°, and accordingly, the base part 100 is located beside the user (for example, on a table edge located on a left or right side distant from the user's arm), not in front of the user, or is fixed to a book shelf, so that even in a case where the base part 100 is located beside the user or diagonally with respect to the user, the articulation 414 is adjusted to the left and right, front and back, or the angle of 360° to allow the recognizing part 400 to be located under his or her chin or around his or her neck. Accordingly, the posture correction device can be used in a right manner.

Figure 10:
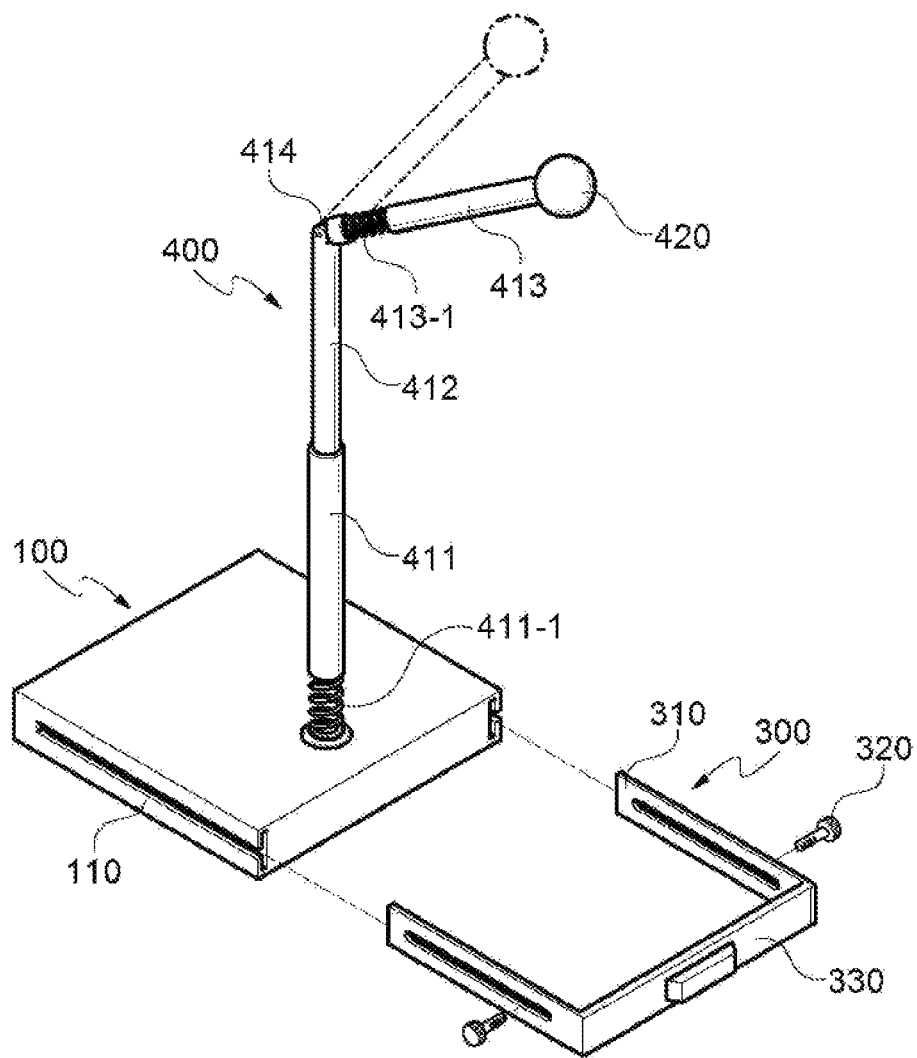
FIG. 10 is a perspective view showing another example of a recognizing part of the posture correction device according to the second embodiment of the present invention.

As shown in FIG. 10, a recognizing part 400 in the posture correction device according to the second embodiment of the present invention includes two erected support tubes 411 and 412 having different diameters from each other, a recognizing support tube 413 whose one side is coupled to the articulation 414 in such a manner as to have a given angle with respect to the support tube 412, and a visual/tactile checking member 420 located on the other side of the recognizing support tube 413.

Further, the recognizing part 400 includes elastic members 411-1 and 413-1 located on the support tube 411 and the recognizing support tube 413 to allow the recognizing part 400 to tilt in one direction by means of an external force and to be returned to its original position if the external force is released.

The elastic members 411-1 and 413-1 are provided on one side of the support tube 411 and the recognizing support tube 413 and are formed of springs.

Figure 11:
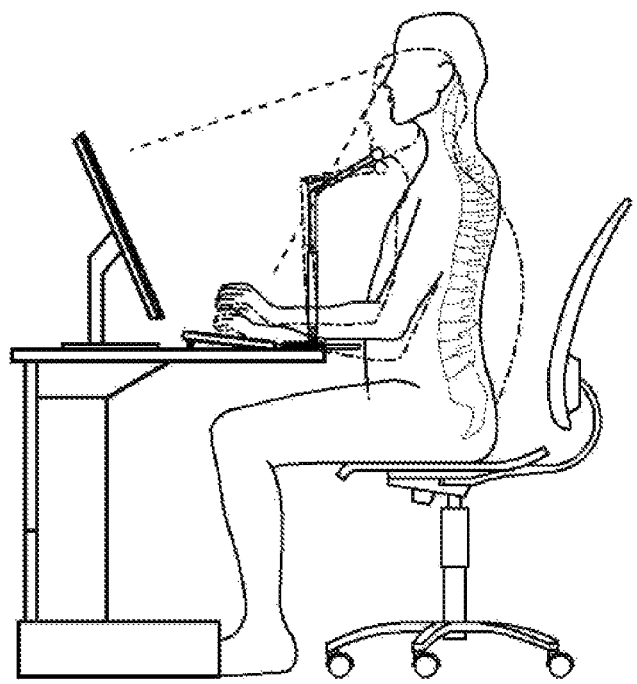
FIG. 11 is a perspective view showing examples of a user's good or bad postures, while another example of the recognizing part of the posture correction device according to the second embodiment of the present invention is being adopted.

Referring to FIG. 11, a user takes a good posture and then adjusts the support tubes 411, 412, and 413 and the articulation 414 to allow the recognizing part 400 to be located under his or her chin or around his or her neck, so that the posture correction device can be used in a right manner.

If it is inevitably necessary for the user to temporarily take a bad posture, the recognizing part 400 can tilt in one direction by means of the user, and if he or she takes a good posture again, the recognizing part 400 can be returned to its original position.

If it is inevitably necessary for the user to do something in a bad posture (for example, in a state of bending his or her head), the recognizing part 400 comes into contact with the user who is bending his or her head, and only if a decree of contact does not interrupt his or her work, accordingly, he or she can recognize his or her bad posture even while concentrating on his or her work.

Figure 12:
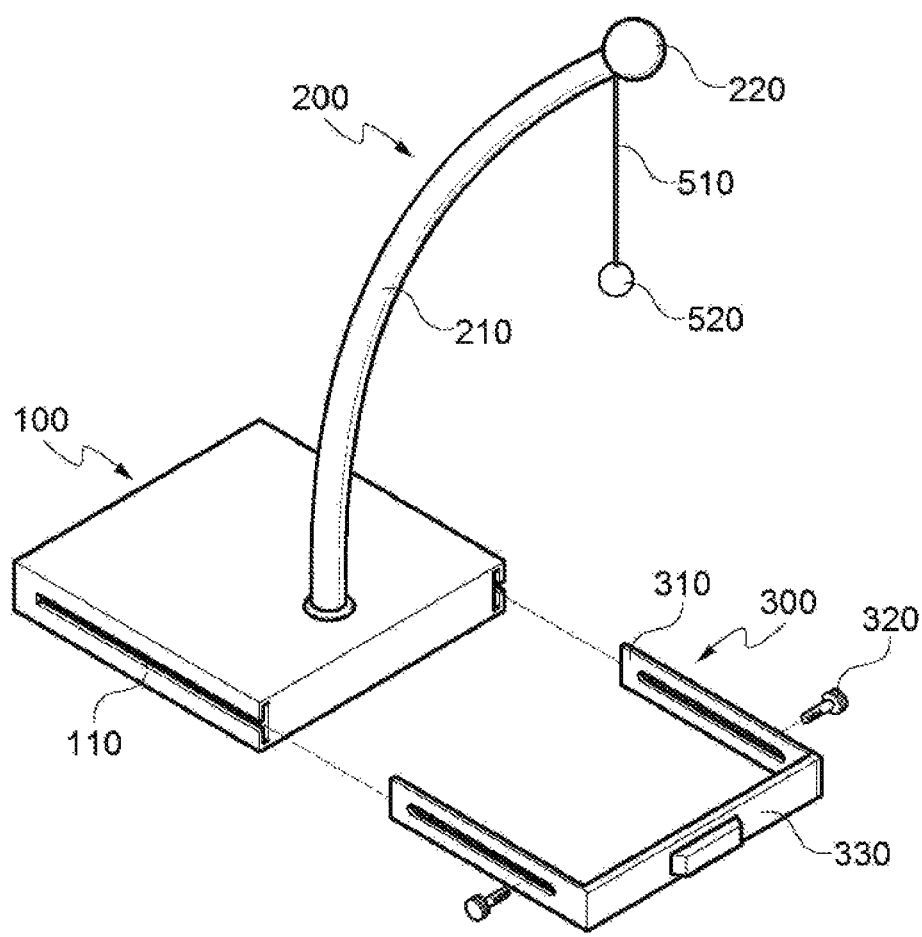
FIG. 12 is a perspective view showing a posture correction device according to a third embodiment of the present invention.

Referring to FIG. 12, a posture correction device according to a third embodiment of the present invention further includes a string or frame 510 connected to the other side end portion of the frame 210 in such a manner as to located under the visual/tactile checking member 220 and an upper body posture checking member 520 located on the end of the string or frame 510.

The upper body posture checking member 520 is provided on the end of the string or frame 510 connected to the other side end portion of the frame 210 in such a manner as to be located under the visual/tactile checking member 220, and if the visual/tactile checking member 220 is located under his or her chin or around his or her neck, the upper body posture checking member 520 can be located on his or her upper body (for example, his or her chest). In some embodiments, the upper body posture checking member 520 is a ball, as shown in FIG. 12.

Only if the upper body posture checking member 520 can be recognized by the visual or tactile sense of the user, it may be freely selected in shape, size, material and color.

Figure 13:
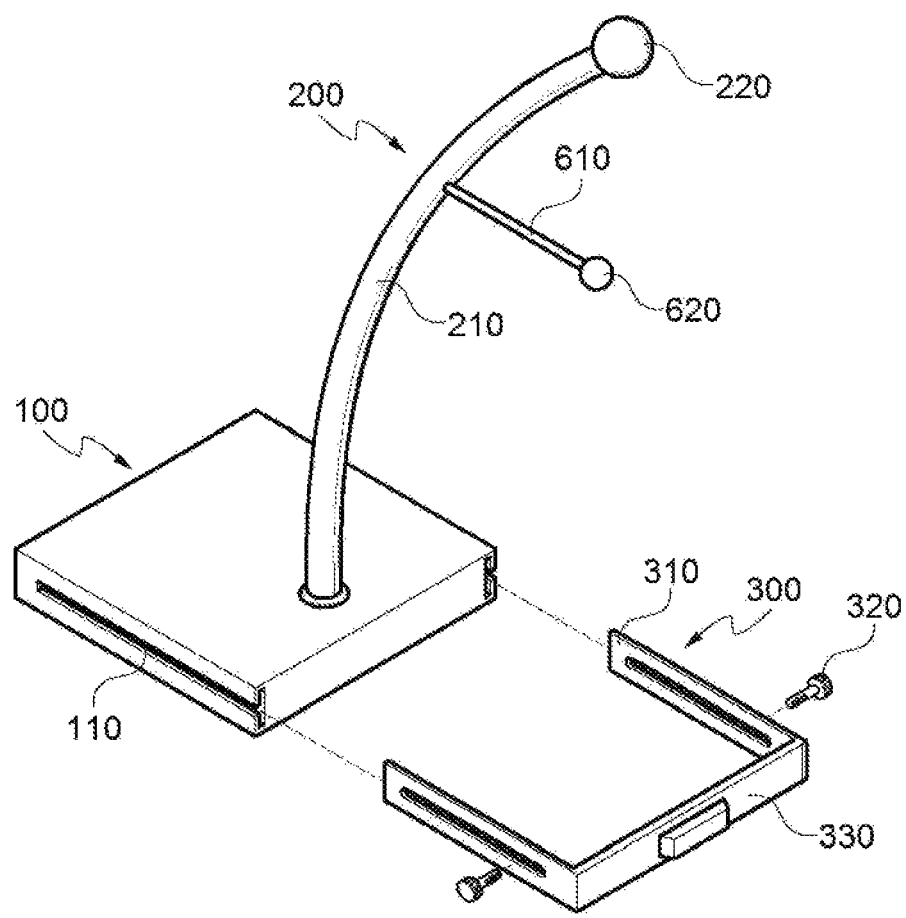
FIG. 13 is a perspective view showing a posture correction device according to a fourth embodiment of the present invention.

Referring to FIG. 13, a posture correction device according to a fourth embodiment of the present invention further includes a contact frame 610 whose one side is coupled to the frame 210 in such a manner as to protrude from the frame 210 toward an upper body of the user and an upper body posture checking member 620 located on the other end portion of the contact frame 610.

The upper body posture checking member 620 is provided on the other end portion of the contact frame 610 whose one side is coupled to the frame 210 in such a manner as to protrude from the frame 210 toward the upper body of the user, and if the visual/tactile checking member 220 is located under his or her chin or around his or her neck, the upper body posture checking member 620 can be located around his or her upper body (for example, his or her chest) under his or her neck.

Only if the upper body posture checking member 620 can be recognized by the visual or tactile sense of the user, it may be freely selected in shape, size, material and color.

Figure 14:
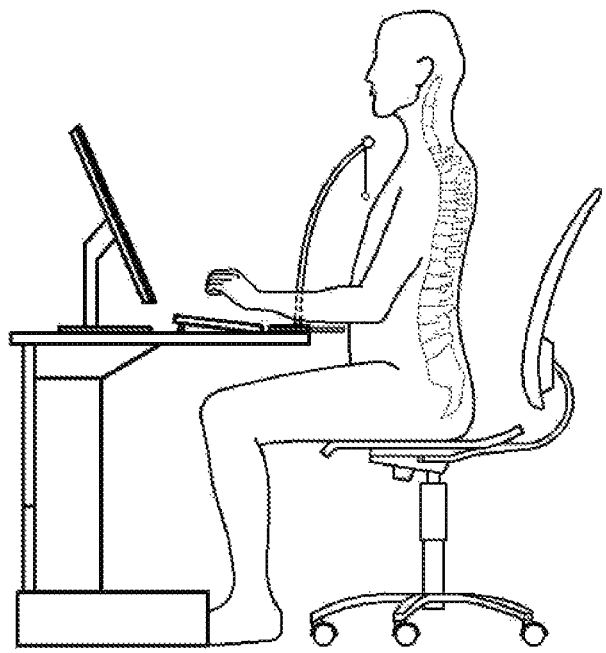
FIG. 14 is a perspective view showing a person's sitting posture on a chair through the posture correction device according to the third embodiment of the present invention.
Figure 15:
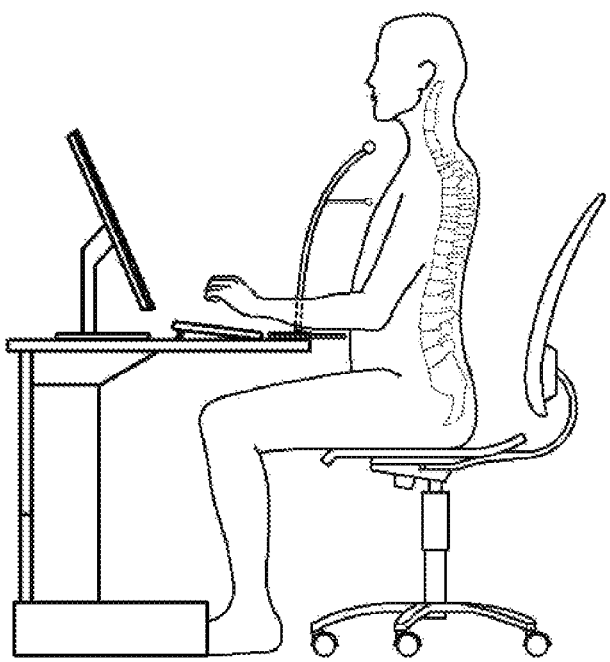
FIG. 15 is a perspective view showing a person's sitting posture on a chair through the posture correction device according to the fourth embodiment of the present invention.

Referring to FIGS. 14 and 15, a user takes a good posture and then adjusts the frame 210 to allow the recognizing part 400 to be located under his or her chin or around his or her neck, so that In this case, the upper body posture checking member 520 is located around the user's chest, and even if no signal is received from the visual/tactile checking member 220 to the user in a state where his or her buttocks excessively push back, it can be checked that the upper body posture checking member 520 does not come into contact with his or her upper body or his or her upper body is not located under the upper body posture checking member 520 (in a vertically downward direction), so that he or she can check a degree of his or her buttocks excessively pushing back.

Figure 16:
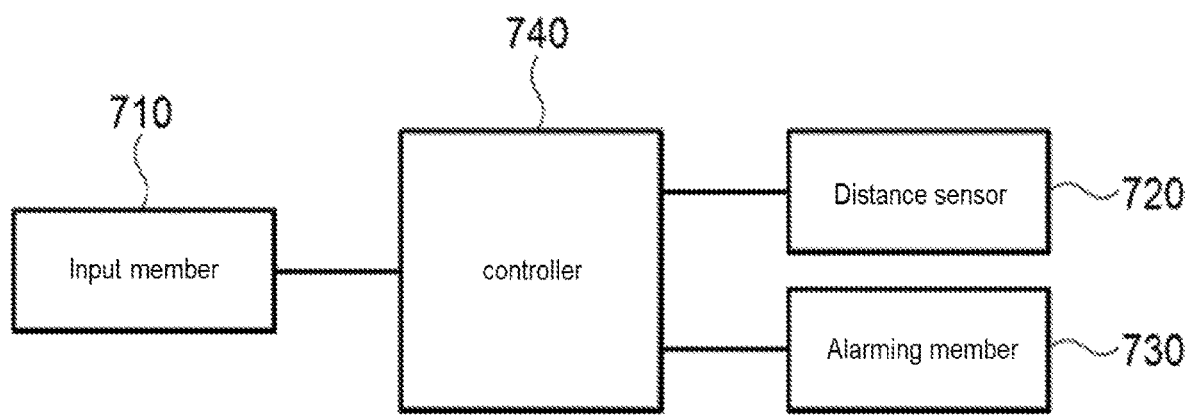
FIG. 16 is a perspective view showing a posture correction device according to a fifth embodiment of the present invention.

Referring to FIG. 16, a posture correction device according to a fifth embodiment of the present invention further includes an input member 710, distance sensors 720, an alarming member 730, and a controller 740.

The input member 710 is located on top of the base part 100 to receive an input from the user, generate an operating signal, and output the operating signal to the controller 740. In detail, the input member 710 receives the input from the user after the visual/tactile checking member 220 has been located under his or her chin or around his or her neck, generates the operating signal, and transfers the operating signal to the controller 740.

The distance sensors 720 are located on the visual/tactile checking member 220 to measure distances from the user's chin, neck, chest or abdomen under the control of the controller 740.

For example, the distance sensors 720 are located on top, user side, or underside of the visual/tactile checking member 220, and the distance sensor 720 located on top of the visual/tactile checking member 220 serves to measure a distance from the user's given body portion.

Further, one of the distance sensors 720 is located on the base part 100 to measure a distance from the user's abdomen.

The alarming member 730 is located on top of the base part 100 to alarm the user's bad posture under the control of the controller 740.

The controller 740 controls the alarming member 730 if the measured distance is longer than a previously set distance.

In detail, if the operating signal is generated through the input member 710 by the user after the visual/tactile checking member 220 has been located under his or her chin or around his or her neck, the controller 740 allows the distance sensors 720 to measure the distance of the visual/tactile checking member 220 from the user's current chin, neck, chest or abdomen, and accordingly, the measured distance is set as a default value. If the measured distances through the distance sensors 720 are longer than the default values and previously set distances, however, the controller 740 determines he or she has a bad posture, so that the controller 740 controls the alarming member 730 to generate a signal sound or light from the alarming member 730.

Further, if the measured distances through the distance sensors 720 are longer than the default values and previously set distances and previously set time also passes, the controller 740 determines he or she has a bad posture, so that the controller 740 controls the alarming member 730 to notify the user of his or her bad posture.

Figure 17:
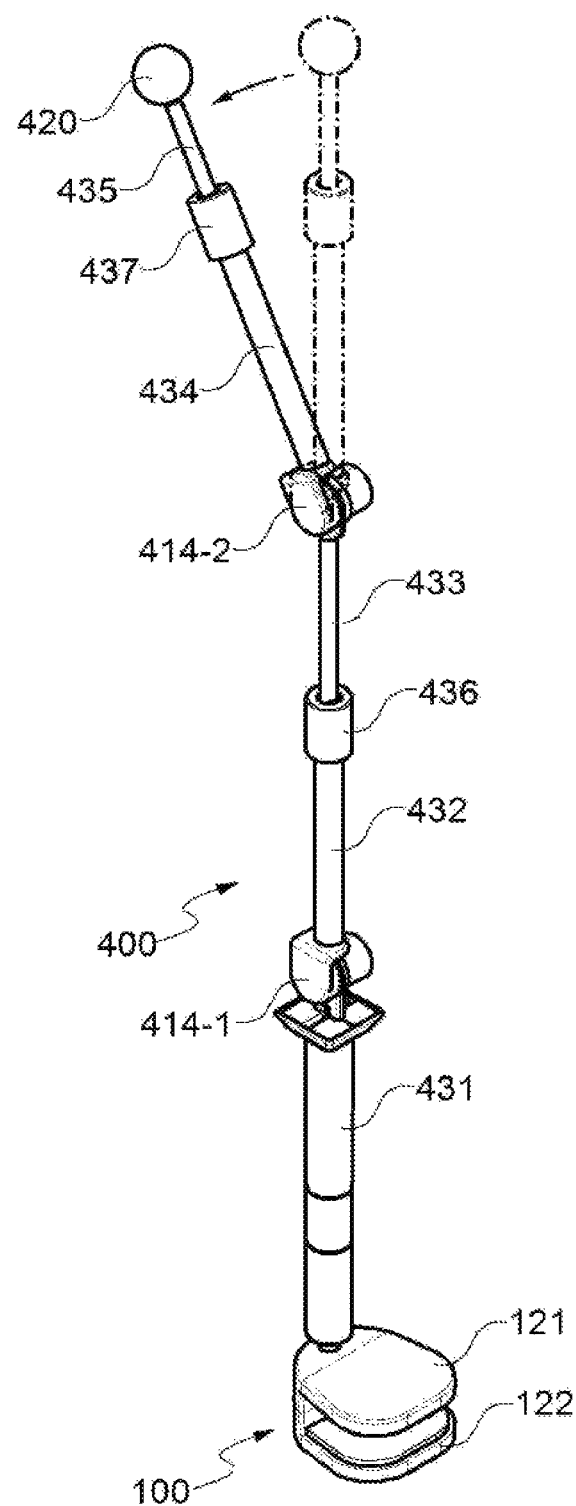
FIG. 17 is a perspective view showing a posture correction device according to a sixth embodiment of the present invention.
Figure 18:
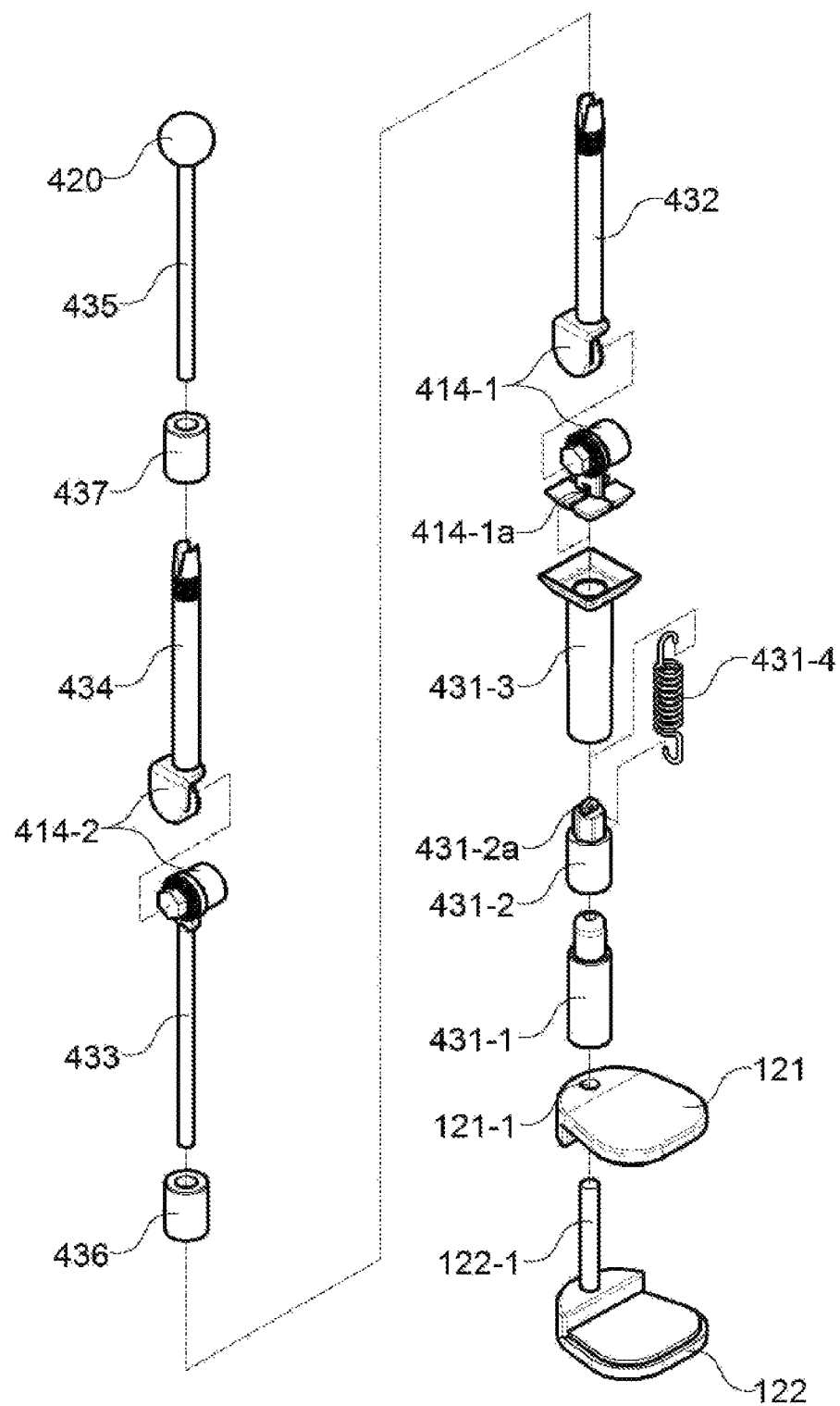
FIG. 18 is an exploded perspective view showing the posture correction device according to the sixth embodiment of the present invention.

Referring to FIGS. 17 and 18, a posture correction device according to a sixth embodiment of the present invention includes a base part 100 constituted of an upper plate 121 and a lower plate 122.

The upper plate 121 has a hole 121-1 formed on a given area thereof, and the lower plate 122 has coupling means 122-1 located on a given area thereof. The coupling means 122-1 passes through the hole 121-1 in such a manner as to be inserted into an insertion groove (not shown) of a main support tube 431 as will be discussed later.

As the coupling means 122-1 of the lower plate 122 passes through the hole 121-1 of the upper plate 121 and is then inserted into the insertion groove of the main support tube 431, the base part 100 can be fixedly coupled to a piece of furniture.

The recognizing part 400 is constituted of a plurality of different-sized support tubes having a shape of a bar having a cylindrical, oval, square, or polygonal section. In this case, the recognizing part 400 has five support tubes 431, 432, 433, 434, and 435, but it is not limited thereto.

Also, the recognizing part 400 has a plurality of articulations. In this case, the recognizing part 400 has two articulations 414-1 and 414-2, but it is not limited thereto.

Referring to FIGS. 17 and 18, the posture correction device according to the sixth embodiment of the present invention includes the recognizing part 400 constituted of the main support tube 431, the two support tubes 432 and 433, and the two recognizing support tubes 434 and 435.

The main support tube 431 and the two support tubes 432 and 433 are connected to each other by means of the first articulation 414-1.

The first articulation 414-1 has a first loop 414-1a adapted to connect one side of an elastic member 431-4 as will be discussed later thereto. One side of the first articulation 414-1 has a shape of a square so that it can be coupled to the other side of a third main support tube 431-4, which has a shape of a square. The two support tubes 432 and 433 and the two recognizing support tubes 434 and 435 are connected to one another by means of the second articulation 414-2.

The main support tube 431 includes a first main support tube 431-1, a second main support tube 431-2, the third main support tube 431-3, and an elastic member 431-4.

The first main support tube 431-1, the second main support tube 431-2, and the third main support tube 431-3 can be connected to one another. The first main support tube 431-1 has the insertion groove formed on one side thereof to insert the coupling means 122-1 of the lower plate 122 thereinto and the other side fittedly connected to the second main support tube 431-2. In this case, the first main support tube 431-1 and the second main support tube 431-2 can be rotatably connected to each other.

If the posture correction device is not used, the recognizing part 400 rotates and is thus kept, thereby optimizing the conveniences of use and the utilization of space.

In a state where the base part 100 and the first main support tube 431-1 are built by the user, further, all parts of the recognizing part 400 except the first main support tube 431-1 are isolated and separately kept, thereby optimizing the conveniences of use and the utilization of space.

In detail, the recognition part 400 rotates or all parts of the recognizing part 400 except the first main support tube 431-1 are isolated and separately kept, without any complete removal of the posture correction device, so that the user can easily stop using the posture correction device.

One side of the second main support tube 431-2 is connected to the first main support tube 431-1, and the other side thereof is connected to the third main support tube 431-3. In this case, the second main support tube 431-2 has a second loop 431-2a formed on the other side thereof in such a manner as to be connected to the other side of the elastic member 431-4.

One side of the third main support tube 431-3 is connected to the second main support tube 431-2, and the other side thereof is connected to the first articulation 414-1. In this case, the other side of the third main support tube 431-3 has a shape of a square.

If the third main support tube 431-3 is spaced apart from the first articulation 414-1 by means of an external force, the third main support tube 431-3 and the first articulation 414-1 can be returned to their original position. If the third main support tube 431-3 and the first articulation 414-1 have the shapes of squares, like this, the first articulation 414-1 can be returned to its original position by means of the elastic member 431-4. In detail, the third main support tube 431-3 and the first articulation 414-1 with the shapes of squares are coupled to each other and returned to their original position, thereby preventing the visual/tactile checking member 420 from tilting or moving to other positions.

On the other hand, the third main support tube 431-3 and the first articulation 414-1 have the shapes of squares, but they are not limited thereto.

Accordingly, the portions of the third main support tube 431-3 and the first articulation 414-1 coupled to each other have the shapes of squares to allow the first articulation 414-1 to be returned to its original position by means of the elastic member 431-4, and in this case, the visual/tactile checking member 420 is prevented from being minutely changed in position.

Further, the third main support tube 431-3 is hollow. The elastic member 431-4 is inserted into the hollow portion of the third main support tube 431-3.

One side of the elastic member 431-4 is connected to the first loop 414-1a of the first articulation 414-1, and the other side thereof is connected to the second loop 431-2a of the second main support tube 431-2.

In detail, the third main support tube 431-3 constantly maintains an elastic force of the elastic member 431-4, and if an external force does not exist, the third main support tube 431-3 prevents the elastic member 431-4 from being bent due to a weight or direction of the recognizing part 400. If a small contact force is generated, the third main support tube 431-3 prevents the elastic member 431-4 from easily swinging.

If an external force is applied, further, the third main support tube 431-3 can tilt in an expectable direction by means of the elastic force constantly maintained, and if the external force is released, the third main support tube 431-3 can be more rapidly and accurately returned to its original position when compared with a case where only the elastic member 431-4 exists without the third main support tube 431-3 and also can stop more quickly residual vibrations when compared with the above-mentioned case.

Even if the posture correction device according to the sixth embodiment of the present invention is deformed by means of the application of the external force, accordingly, it can be returned to its original position by means of the elastic member 431-4, so that the visual/tactile checking member 420 can be fixed to a given position. Further, the elastic member 431-4 can prevent the third main support tube 431-3 from being damaged and broken by means of the external force.

The two support tubes 432 and 433 may have different diameters from each other. The two support tubes 432 and 433 are constituted of the first support tube 432 connected to the first articulation 414-1 and the second support tube 433 fitted to the first support tube 432, and they are adjusted in height in up and down directions.

On the other hand, the first articulation 414-1 has a pivot structure, but it may have known structures freely, without being limited thereto.

Further, first adjusting means 436 is provided to adjust a coupled height of the two support tubes 432 and 433.

On the other hand, in this case, the first adjusting means 436 is rotatingly fastened along a screw thread formed on the first support tube 432 to fix the coupled height of the two support tubes 432 and 433, but it may be not limited thereto.

The two recognizing support tubes 434 and 435 may have different diameters from each other. The two recognizing support tubes 434 and 435 are constituted of the first recognizing support tube 434 connected to the second articulation 414-2 and the second recognizing support tube 435 fitted to the first recognizing support tube 434, and they are adjusted in height in up and down directions.

The visual/tactile checking member 420 is located on the second recognizing support tube 435. On the other hand, the second articulation 414-2 has a pivot structure, but it may have known structures freely, without being limited thereto.

Further, second adjusting means 437 is provided to adjust a coupled height of the two recognizing support tubes 434 and 435. In this case, the second adjusting means 437 is rotatingly fastened along a screw thread formed on the first recognizing support tube 434 to fix the coupled height of the two recognizing support tubes 434 and 435, but it may be not limited thereto.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

EXPLANATIONS OF REFERENCE NUMERALS
IN THE DRAWINGS

10: posture correction device
100: base part
110: slide slot
121: upper plate
122: lower plate
123: fastening means
124: screw insertion hole
200, 400: recognizing part
210: frame
220, 420: visual/tactile checking member
300: contact part
310: slider
320: slider fixing means
330: abdomen contact member
411, 412, 413, 431, 432, 433, 434, 435: support tube
414: articulation
411-1, 411-3: elastic member
510: string or frame
520, 620: upper body posture checking member
610: contact frame
710: input member
720: distance sensor
730: alarming member
740: controller

What is claimed is:

1. A posture correction device comprising:
a base part that can be freely fixed to a predetermined structure desired by a user; and
a recognizing part having a frame whose one side is coupled to the base part in such a manner as to allow one or more of a height and an angle to be adjusted and adapted to be fixedly located under a user's chin or around the user's neck according to his or her posture to be recognized visually and tactilely,
wherein the recognizing part comprises:
support tubes coupled to the base part;
a recognizing support tube connected to the support tubes through an articulation; and
at least one or more elastic members tilting in one direction by an action of an external force and returned to original positions thereof if the external force is released, and
wherein the elastic member is inserted into a hollow formed in the support tube or recognizing support tube, connected to the base part or other support tubes to provide elastic restoring force,
allowing the user to recognize a relative position with the recognizing part fixed under the user's chin or around the user's neck through height and angle adjustments, determine incorrect posture while seated,
and naturally guide the user to correct posture through recognition without physical contact.

2. The posture correction device according to claim 1, wherein the recognizing part further comprises a visual/tactile checking member coupled to the other side end portion of the frame in such a manner as to be located under the user's chin or around the user's neck and to be thus recognized visually or tactilely according to the user's posture.

3. The posture correction device according to claim 2, wherein the recognizing part further comprises an upper body posture checking member connected to the frame in such a manner as to be located around the user's upper body under the user's neck if the visual/tactile checking member is located under the user's chin or around the user's neck.

4. The posture correction device according to claim 3, wherein the recognizing part further comprises:
a string or frame connected to the other side end portion of the frame in such a manner as to located under the visual/tactile checking member; and
an upper body posture checking member provided on the end of the string or frame in such a manner as to be located around the user's upper body under the user's neck if the visual/tactile checking member is located under the user's chin or around the user's neck.

5. The posture correction device according to claim 3, wherein the recognizing part further comprises:
a contact frame whose one side is coupled to the frame in such a manner as to protrude toward the user's upper body; and
an upper body posture checking member provided on the other side end portion of the contact frame in such a manner as to be located around the user's upper body under the user's neck if the visual/tactile checking member is located under the user's chin or around the user's neck.

6. The posture correction device according to claim 2, further comprising:
a distance sensor located on the visual/tactile checking member to measure a distance from the user;
an alarming member for generating an alarm to the user; and
a controller for controlling the alarming member on the basis of the measured distance through the distance sensor.

7. The posture correction device according to claim 1, further comprising a contact part coupled to one side of the base part in such a manner as to protrude toward the user's abdomen.

8. The posture correction device according to claim 7, wherein the contact part is slidably coupled to both sides of the base part in such a manner as to be adjusted in a length protruding from the base part toward the user's abdomen.

9. The posture correction device according to claim 8, wherein the contact part comprises:
slide slots formed on both sides of the base part in a longitudinal direction of the base part;
one pair of sliders slidable forward and backward along the slide slots;
slider fixing means adapted to fix one pair of sliders to the slide slots; and
an abdomen contact member adapted to connect ends of one pair of sliders to each other in such a manner as to come into contact with the user's abdomen.

10. The posture correction device according to claim 1, wherein the recognizing part further comprises a main support tube whose one side is coupled to the base part and the other side is coupled to an articulation to have a given angle with respect to the frame, the main support tube comprising:
a first main support tube coupled to the base part;
a second main support tube coupled to the first main support tube; and
a third main support tube coupled to the second main support tube and having a hollow portion adapted to insert an elastic member thereinto, the elastic member being inserted into the hollow portion of the third main support tube in such a manner as to allow one side thereof to be connected to the articulation and the other side thereof to be connected to the second main support tube.

11. The posture correction device according to claim 10, wherein the other side of the third main support tube has one shape of a sphere, triangle, and square, and the articulation has a corresponding shape to the other side of the third main support tube in such a manner as to be seated onto the other side of the third main support tube.

12. The posture correction device according to claim 1, further comprising coupling means located rotatable to left and right sides on the base part in such a manner as to be coupled to one side of the frame to allow the recognizing part to be pivoted in left and right directions with respect to the user.

13. The posture correction device according to claim 1, wherein the base part has a suction pad located on the underside thereof.

14. The posture correction device according to claim 1, wherein the base part comprises:
an upper plate coupled to the recognizing part;
a lower plate located on the underside of the upper plate; and
fastening means for fastening the upper plate and the lower plate to a piece of furniture.

15. The posture correction device according to claim 1, wherein the recognizing part is made of a flexible material capable of being adjusted in height and angle thereof.

16. The posture correction device according to claim 1, wherein the recognizing part is constituted of a plurality of different-sized support tubes capable of being adjusted in height thereof.

17. The posture correction device according to claim 1, wherein the recognizing part is coupled to the base part in such a manner as to allow one side thereof to be detachably mounted on the base part.

* * * * *